(12) United States Patent
Stevens et al.

(10) Patent No.: US 6,699,279 B2
(45) Date of Patent: Mar. 2, 2004

(54) EXPANDABLE SPACE FRAME

(75) Inventors: Walter J. Stevens, Fairfax, VA (US); George S. Springer, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 10/147,391

(22) Filed: May 15, 2002

(65) Prior Publication Data

US 2002/0183833 A1 Dec. 5, 2002

Related U.S. Application Data

(63) Continuation of application No. 09/674,185, filed as application No. PCT/US99/09383 on Apr. 30, 1999, now Pat. No. 6,497,274, which is a continuation-in-part of application No. 09/070,476, filed on Apr. 30, 1998, now abandoned.

(51) Int. Cl.[7] .................................................. A61F 2/06
(52) U.S. Cl. ...................... 623/1.15; 623/1.16; 623/1.22
(58) Field of Search .............................. 623/1.15, 1.16, 623/1.2, 1.22; 606/213

(56) References Cited

U.S. PATENT DOCUMENTS

| | | | |
|---|---|---|---|
| 5,102,417 A | | 4/1992 | Palmaz |
| 5,334,217 A | * | 8/1994 | Das ............................ 606/213 |
| 5,443,500 A | | 8/1995 | Sigwart |
| 5,681,345 A | | 10/1997 | Euteneuer |
| 5,702,419 A | | 12/1997 | Berry et al. |
| 5,707,387 A | | 1/1998 | Wijay |
| 5,707,388 A | | 1/1998 | Lauterjung |
| 5,843,170 A | | 12/1998 | Ahn |
| 5,843,176 A | * | 12/1998 | Weier ............................. 623/1 |
| 6,245,102 B1 | * | 6/2001 | Jayaraman ................. 623/1.15 |
| 6,327,772 B1 | * | 12/2001 | Zadno-Azizi et al. ......... 29/557 |
| 6,497,724 B1 | * | 12/2002 | Stevens et al. ............. 623/1.15 |
| 6,508,833 B2 | * | 1/2003 | Pavcnik et al. ............ 623/1.15 |

OTHER PUBLICATIONS

Fontaine et al. (1997) "Vascular stent prototype: in vivo swine studies." *J Vasc Interv Radiol.*, vol. 8(1 Pt 1):107–11.

Hong et al. (1997) "Acute and chronic effects of self-expanding nitinol stents in porcine coronary arteries." *Coron Artery Dis.*, vol. 8(1):45–8.

Palmaz (1992) "Intravascular stenting: from basic research to clinical application." *Cardiovasc Intervent Radiol.*, vol. 15(5):279–84.

Sniderman (1996) "Noncoronary vascular stenting." *Prog Cardiovasc Dis.*, vol. 39(2):141–64.

Wong et al. (1996) "Early clinical experience with the Multi–Link coronary stent." *Cathet Cardiovasc Diagn.*, vol. 39(4):413–9.

Fontaine, Arthur B. et al., "Vascular stent Prototype: In Vivo Swine Studies[1]," *Journal of Vascular and Interventional Radiology* (1997) vol. 8, No. (1):107–111.

(List continued on next page.)

*Primary Examiner*—Bruce Edward Snow
(74) *Attorney, Agent, or Firm*—Pamela J. Sherwood; Bozicevic, Field & Francis LLP

(57) ABSTRACT

An expandable space frame is manufactured by linking a plurality of flexible joints through spacing arms to form a closed structure. The spacing arms are sterically offset, linking the bottom of one joint to the top of the next joint in an stepwise fashion. The offset allows the frame to be collapsed with minimal steric hindrance between the centered joints. This lack of steric hindrance permits a very high ratio of the expansion to compression diameters for the frame. The space frame forms the basis for different types of stents. A spiral frame, or a series of individual frames are linked to each other to form a luminal stent, or are linked to longitudinal struts to form the support structure for a stent. The stents formed from the expandable space frame can be designed to have a number of additional features as set forth herein.

12 Claims, 14 Drawing Sheets

OTHER PUBLICATIONS

Hong, Mun K., et al., "Acute and Chronic Effects of Self–Expanding Nitinol Stents In Procine Coronary Arteries," *Coronary Artery Disease* (Jan. 1997) vol. 9, No. (1):45–48.

Palmaz, Julio C., "Intravasular Stenting: From Basic Research to Clinical Application," *Cardiovase Intervent Radiol* (1992) vol. 15:279–284.

Sniderman, Kenneth W., "Noncoronary Vascular Stenting," *Progress in Cardiovascular Diseases* (Sep./Oct. 1996) vol. XXXIX. No. (2): 141–164.

Wong, Phillip, et al., "Early Clinical Experience With the Multi–Link Coronary Stent," *Catheterization and Cardiovascular Diagnosis* (1996) vol. 39:413–419.

* cited by examiner

EXPANDABLE SPACE FRAME

This application is a continuation of Ser. No. 09/674,185, filed on Oct. 27, 2000, now U.S. Pat. No. 6,497,724 which is a 371 of PCT/US99/09383, filed Apr. 30, 1999 which is a CIP of Ser. No. 09/070,476 Filed Apr. 30, 1998 now abandoned.

BACKGROUND OF THE INVENTION

In a variety of situations, it is desirable to have a radially stiff framework that can be collapsed to a very small diameter. The ability to expand five to ten-fold or greater has great utility in applications where space is at a premium. One use for an expandable space frame is in the construction of luminal stents, where the term "stent" is genericaly used to describe structural devices that support living tissues.

Stents are implanted in a body lumen for treating abnormal conditions. For example, these devices have found use in maintaining the patency of collapsing and partially occluded blood vessels, particularly to prevent acute closure and restenosis after a vessel has been enlarged by angioplasty. These devices have also been used to reinforce other body lumens, such as the urinary tract, the bile tract, the intestinal tract, and the tracheobronchial tree.

Conventional stents are cut from a tube or formed from a wire that has been bent back and forth in a zig-zag pattern and wound in a circumferential direction to form one or more loops of a pre-determined circumference. Typically, the stent is radially expandable from a collapsed condition. It is desirable to minimize the diameter of the collapsed stent so that it can be delivered as unobtrusively as possible through the vasculature. Once in position it is expanded to the predetermined size, to support and reinforce the lumen.

The stent is normally inserted in the collapsed condition by a catheter during intraluminal delivery to the repair site. Once properly located, the stent is removed from the catheter and radially expanded until its circumference firmly contacts the interiorwall of the lumen. Usually the radial expansion is caused by the dilation of an angioplasty balloon placed axially within the stent. Alternatively, the stent may be made from a shape memory metal, whereby the stent will automatically assume its expanded circumference as its temperature increases upon implantation, or stents can be made that expand through spring action.

An important attribute of the stent is its ability to provide radial support. This capability is a concern not only where the stent is being used to maintain the patency of the lumen in which it is located, but also where the stent is being used in conjunction with a prosthetic graft to keep the graft open and to hold it at the location at which it is implanted.

The patent literature contains descriptions of many different stent designs. A few of the more recent patents include U.S. Pat. No. 5,702,419, "Expandable, Intraluminal Stent"; U.S. Pat. No. 5,707,388, "High Hoop Strength Intraluminal Stent"; U.S. Pat. No. 5,707,387, "Flexible Stent"; and U.S. Pat. No. 5,681,345, "Sleeve Carrying Stent"; Palmaz, U.S. Pat. No. 5,102,417, "Expandable intraluminal graft, and method and apparatus for implanting an expandable intraluminal graft"; and Sigwart, U.S. Pat. No. 5,443,500, "Intravascular stent".

Scientific reviews of stent design and function may be found in Wong et al. (1996) *Catheterization and Cardiovascular Diagnosis* 39:413–419; Sniderman (1996) Progress in Cardiovascular Diseases, vol. XXXIX:141–164. Fontaine and dos Passos (1997) *Journal of Vascular and Interventional Radiology* 8:107–111 present an example of pre-clinical analysis for a prototype stent. Hong et al. (1997) *Coronary Artery Disease* 8:45–48, describe pre-clinical use of a self-expanding nitinol stent.

Features desirable in a stent are reviewed by Palmaz (1992) *Cardiovasc. Intervent. Radiol.* 15:279–284. A highly desirable stent would combine a high expansion ratio with radial stiffness and lengthwise flexibility to facilitate insertion and/or conform to curves of the vessel once in place. The present invention provides this and other useful features.

SUMMARY OF THE INVENTION

An expandable space frame linking a plurality of flexible joints, e.g. springs; riveted or pinned joints; etc., joined through spacing arms to form a closed structure, e.g. circle, ellipse, rectangle, etc. is provided. The spacing arms are sterically offset, linking the bottom of one junction to the top of the next junction in an upwards stepwise fashion for a portion of the circle, and then reversing the steps to go down. The offset allows the frame to be collapsed with minimal steric hindrance, which permits a very high ratio of the expansion to compression diameters for the frame. The space frame forms the basis for different types of stents. A series of individual frames are linked to each other to form a stent. Alternatively, two or more frames are linked to longitudinal struts to form the support structure for a stent. The stents formed from the expandable space frame can be designed to have a number of additional features as set forth herein.

DETAILED DESCRIPTION OF THE EMBODIMENTS

Figure 1A:
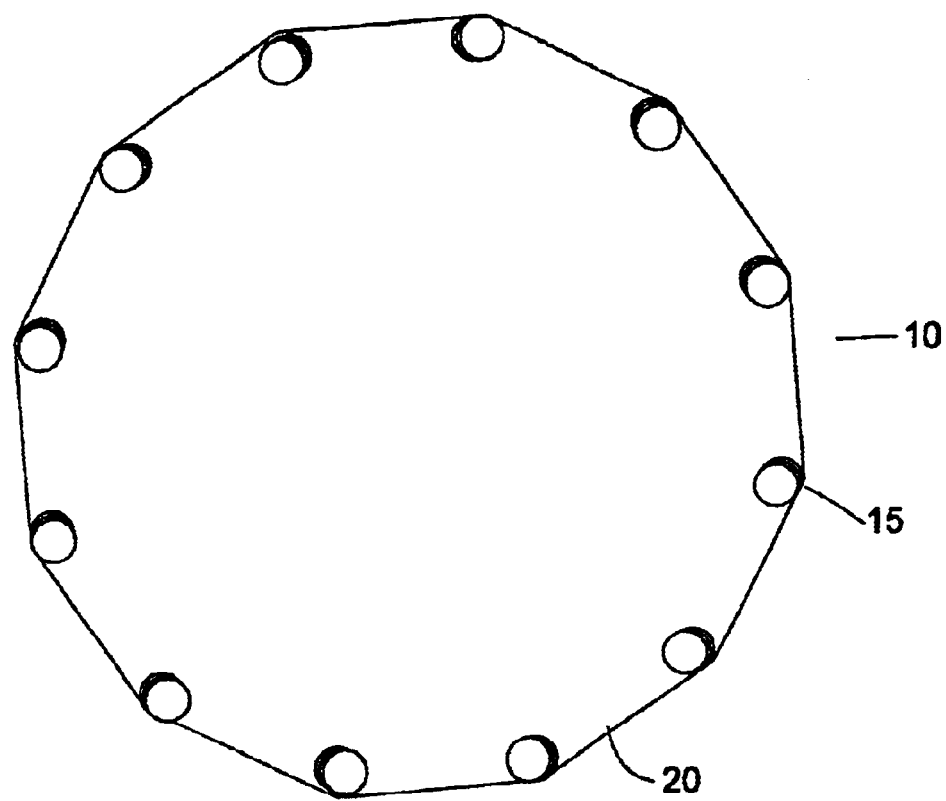
FIG. 1A shows a top view of a circular space frame with spring junctions, in the expanded configuration.

An expandable space frame is provided, comprising a plurality of flexible joints, e.g. springs; riveted or pinned joints; etc., joined through spacing arms to form a closed structure, e.g. circle, ellipse, rectangle, etc. FIG. 1A illustrates a circular frame having spring joints. The frame is shown with all the spring joints on the inside of the frame. An alternative configuration has all the spring joints outside of the frame. Where the spring joints are partially outside and partially inside, the coil direction of the springs will change at the points where the inside/outside orientation changes. The frame is also shown with arms of equal length, although for some purposes it will be desirable to vary the length of the arms.

The frame 10 is comprised of spacing arms 20 and joints 15. Each joint has two spacing arms, one at the top of the joint 20 and one at the bottom 25, which extend from roughly the same point on the spring. The spacing arms form the linkage between joints, linking the bottom of one spring to the top of the next spring in a stepwise fashion. When linked, the spacing arms form a closed structure.

Figure 1B:
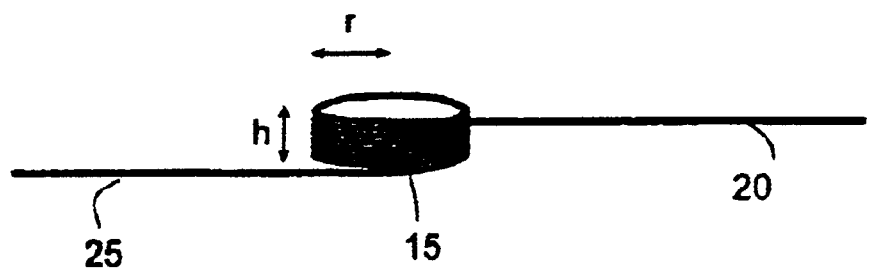
FIG. 1B shows a detail of the spacing arms and a spring junction in the expanded (anti-parallel) configuration.

Depending on whether the frame is in the collapsed or expanded configuration, the two spacing arms are differently oriented with respect to the attached flexible joint. The arms can be in an expanded configuration where the two arms face outward from the joint in a roughly antiparallel orientation, shown in FIG. 1B, where upper arm 20 is antiparallel to the lower arm 25. It will be understood by one of skill in the art that the top arm of one joint is the bottom arm of the adjoining joint. The designation as "upper" or "lower" is arbitrary, and merely used to clarify the geometric relationships in the frame. In a compressed configuration, the two arms face outward from the joint in a roughly parallel orientation, shown in FIG. 2D. The joint 15 is tightened so that the upper arm 20 is parallel to the lower arm 25.

Figure 10A:
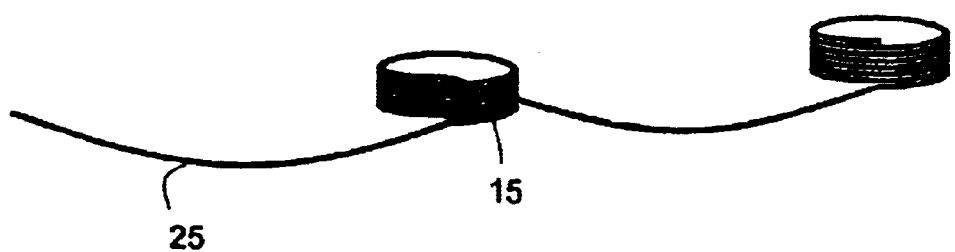
FIG. 10A is a side view of the flexible arm embodiment in an elongated configuration.
Figure 10B:
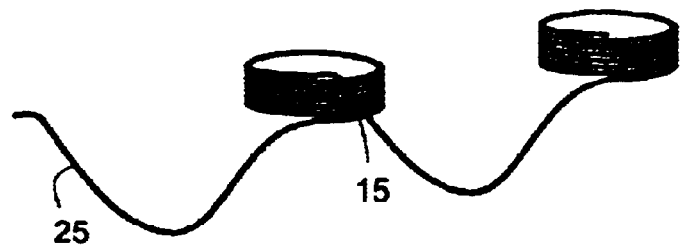
FIG. 10B is a side view of the flexible arm embodiment is a contracted position.

In one embodiment of the invention, as shown in FIGS. 10A and 10B, the arms 25 are flexible, and can contract and elongate to provide variable spacing between the joints. The arms can be made to elongate from a contracted position by spring action, memory alloy, etc., or through the use of a balloon catheter.

Figure 2A:
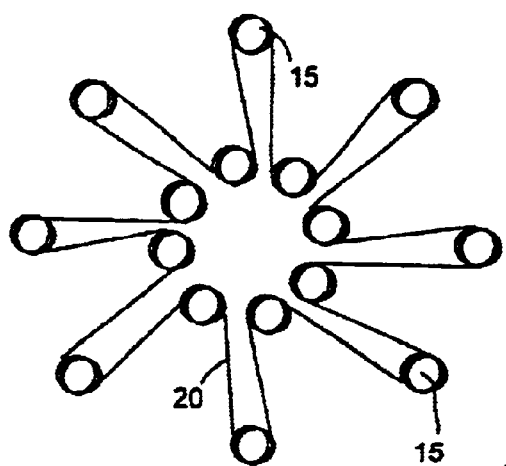
FIG. 2A shows a top view of a circular space frame in a semi-compressed configuration.
Figure 2B:
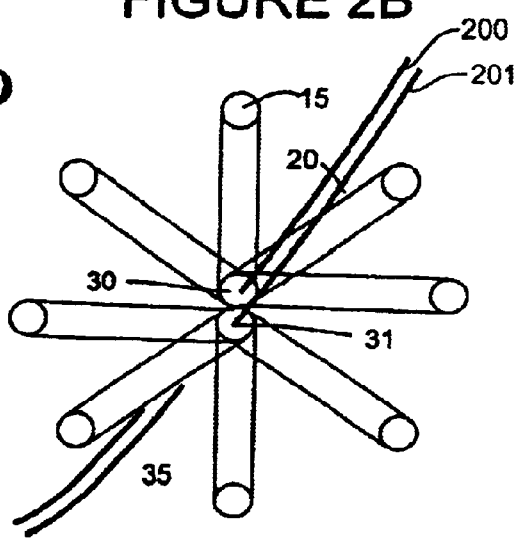
FIG. 2B is the space frame in a fully compressed configuration.
Figure 2C:
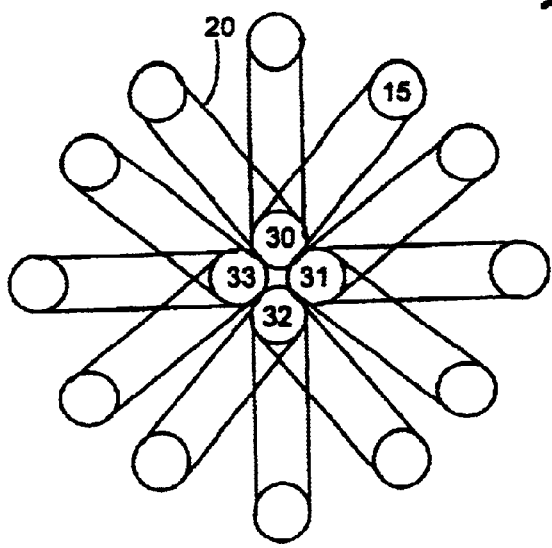
FIG. 2C shows a the compressed configuration of a space frame with four changes in offset.
Figure 2D:
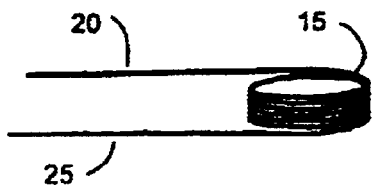
FIG. 2D is a detail of the spacing arms and a spring in the compressed (parallel) configuration.

In the expanded state, shown in FIG. 1A, all of the joints are on the perimeter of the frame, with the spacing arms forming the circumference of the frame. In a compressed configuration 35, the joints alternate: a joint with both arms facing inwards (toward the center of the circle) with a joint with both arms facing outwards (towards the perimeter of the circle). FIGS. 2A and 2B show the compression of the frame, with FIG. 2A partially compressed and FIG. 2B in the fully compressed configuration. Alternating joints 15 are drawn to the center of the frame. In the compressed configuration half the joints are located in the centers 30 and 31, and half are on the perimeter. For the closed frame, the inner joints will not all come together. As shown in FIG. 2B, there will be at least two joints that are side by side, 30 and 31, for a frame that has two changes in offset direction (as described below). If there are four changes of offset direction, shown in FIG. 2C then 4 joints, 30, 31, 32, and 33 will meet in the center.

Figure 3A:
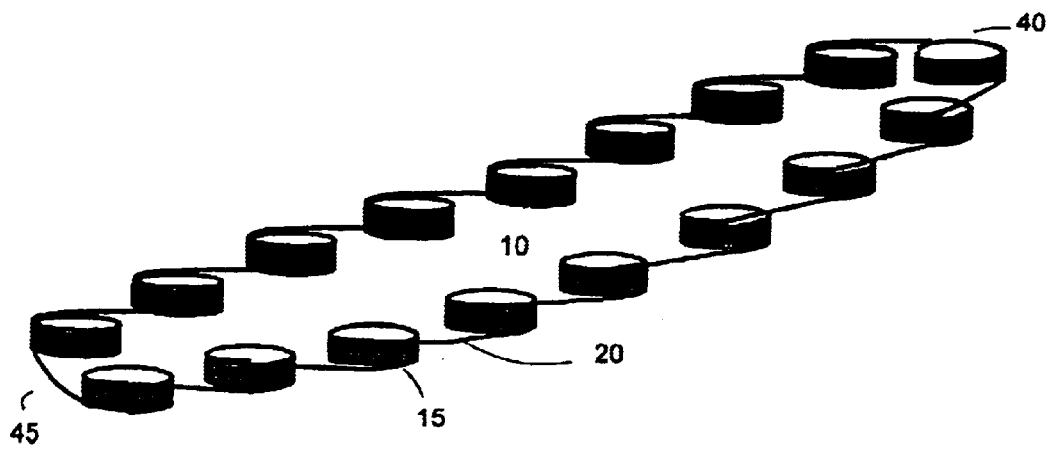
FIG. 3A is a view of the space frame drawn to show the steric offset of the spacing arms between the spring junctions.

FIG. 3 shows a side view of the space frame 10 to illustrate the geometry of the spacing arms. The spacing arms 20 are sterically offset, linking the bottom of one joint 15 to the top of the next joint in a stepwise fashion, and then reversing the steps with a change in offset direction. The "up staircases" may comprise half of the frame, with a "down staircases" comprising the other half of the frame. Alternatively, one quarter of the frame can be an "up staircase", followed by one quarter as a "down staircase"; and so on.

Figure 3B:
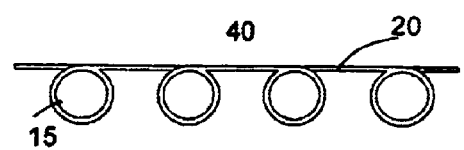
FIG. 3B is a top view showing the point at which the steric offset changes direction, and the coil of the springs is changed.
Figure 3C:
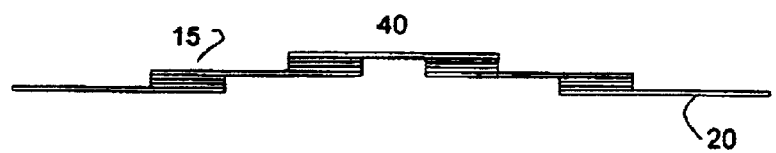
FIG. 3C shows the same object in a side view.

The offset direction for a half circle staircase changes at two points, 40 and 45. Where the joints are spring joints, the direction of the spring winding changes at these points. FIG. 3B and FIG. 3C provide a side and top view at the change in offset direction 40, illustrating the change in the winding of the springs 15.

Figure 11A:
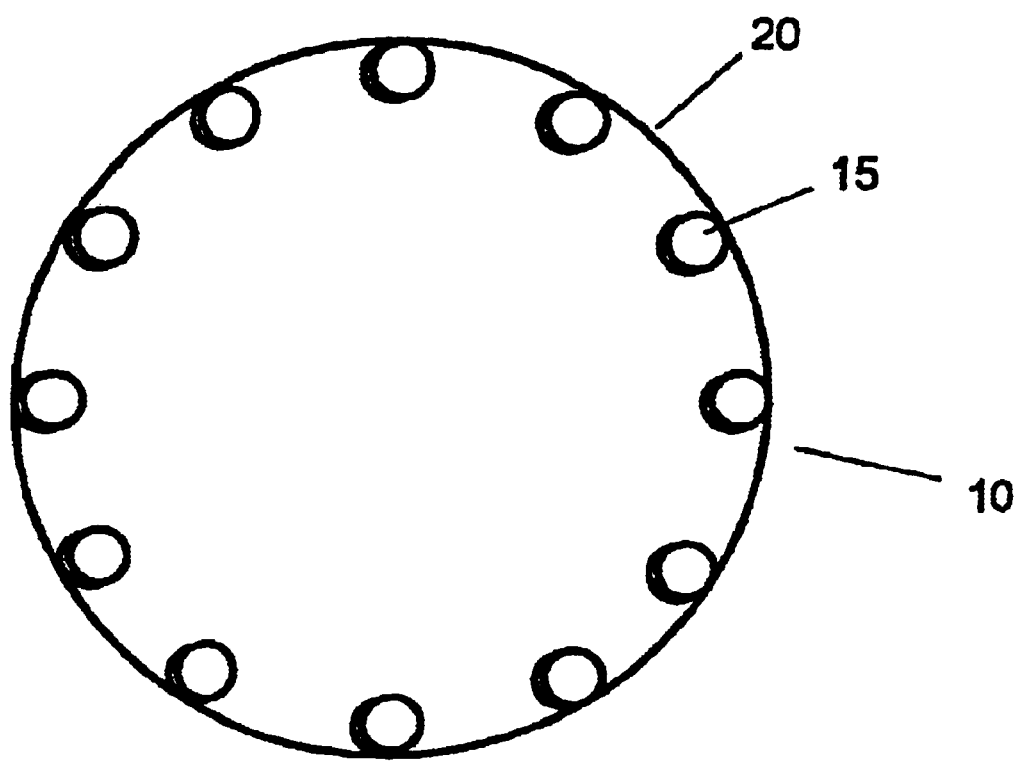
FIG. 11A and FIG. 11B are side and top views of a spiral structure embodiment of the space frame.
Figure 11B:
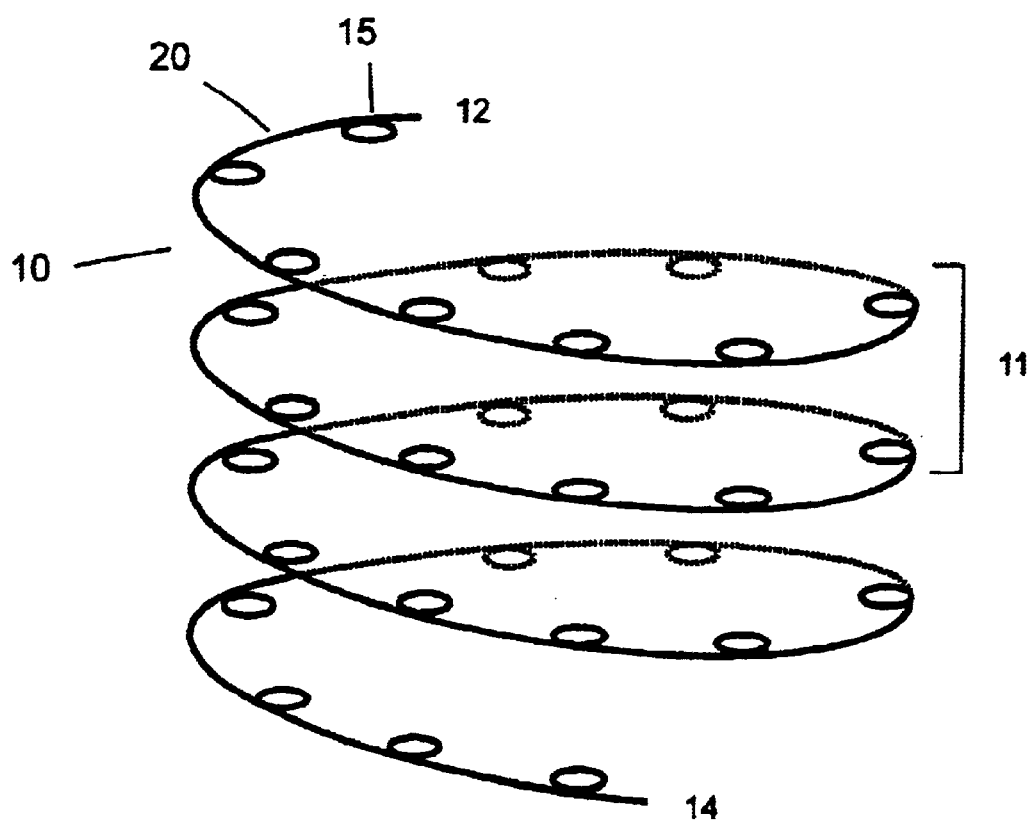

In an alternate embodiment of the invention, a spiral structure is formed by the continuous procession of spacing arms in a single stepwise direction. The side view of this embodiment is shown in FIG. 11A, depicting the frame 10, comprised of spacing arms 20 and joints 15. A top view is shown in FIG. 11B of the frame 10. Each circular segment of the frame may be referred to as a spiral unit 11. The number of spiral units is usually at least about 3, more usually from about 10–20, and usually not more than about 200. Unlike a closed frame, the spiral frame also comprises two ends, 12 and 14. The ends may be left free, or optionally are connected with a longitudinal strut. Alternatively, the free ends are covered in a suitable material, e.g. as shown in FIG. 9 for a stent. The cover may be of a flexible material, or a rigid coating.

Figure 11C:
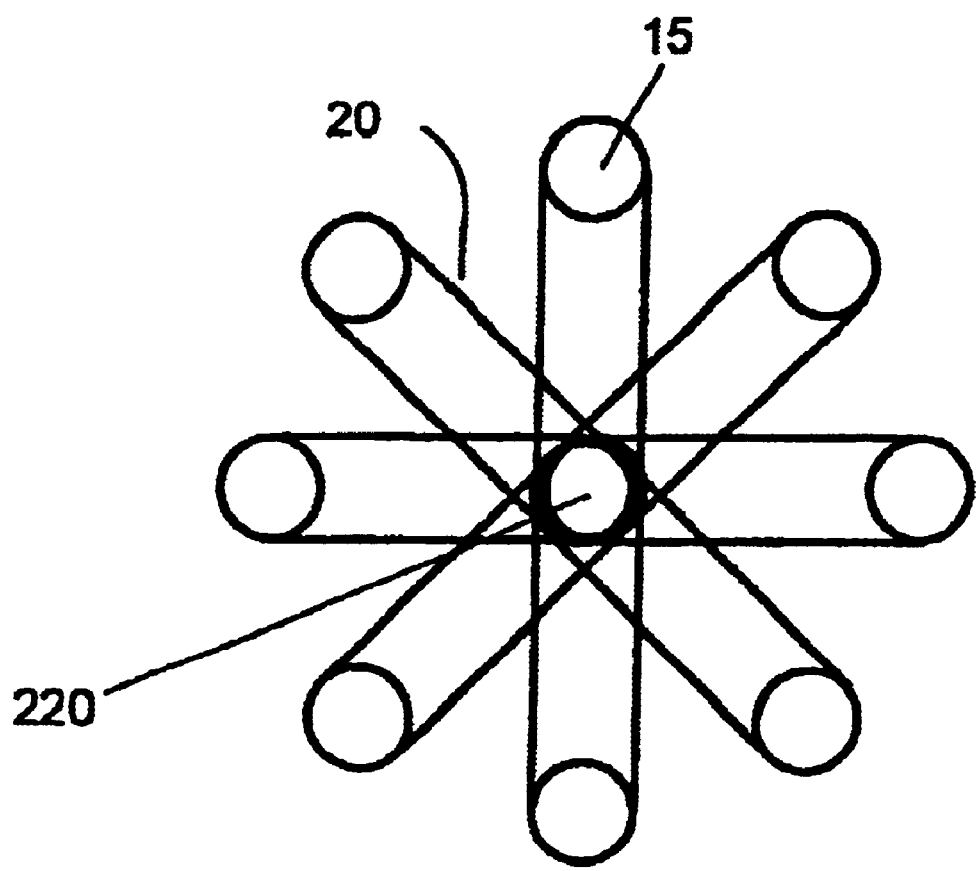
FIG. 11C is a top view of the collapsed spiral structure.

The overall length of the spiral structure is determined by the length of the offset of each spacing arm, the number of flexible joints in each complete turn of the spiral, and the total number of complete turns in the spiral. Because there is no change in offset direction of the spacing arms in the spiral structure, all of the inner joints will come together when the structure is collapsed, as shown in FIG. 11C.

The offset allows the frame to be in a collapsed configuration with minimal steric hindrance between the centered joints. This lack of steric hindrance permits a very high ratio of the expansion to compression diameters for the frame. The degree of expansion will be at least 3-fold, usually at least about 5-fold, and preferably at least about 10-fold, or higher.

The joints between the spacer arms may be any joining mechanism that is flexible enough to accommodate the collapsed and expanded configurations. The joint may be a spring, as shown in FIGS. 1 and 2. The use of springs allow the frame to be self-expanding: the frame is held in a compressed state until expansion is desirable, then the hold is released and the frame springs to the expanded configuration. Alternatively, pinned or riveted joints may be used.

Figure 4A:
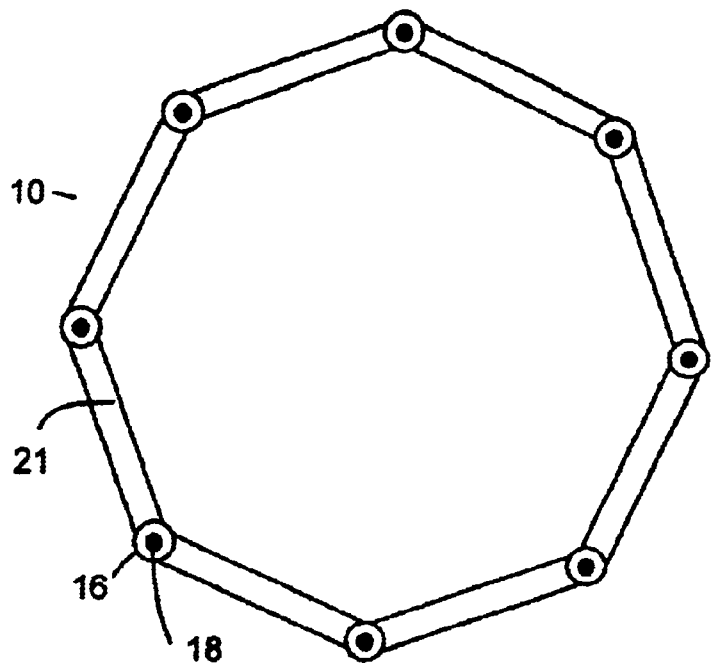
FIG. 4A shows a top view of a frame using pinned joints.
Figure 4B:
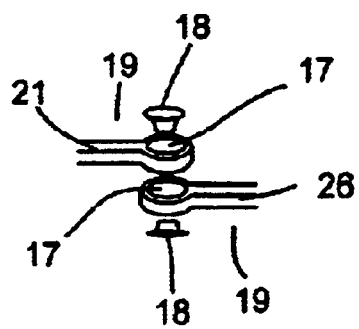
FIG. 4B is a detail of a pinned joint.
Figure 4C:
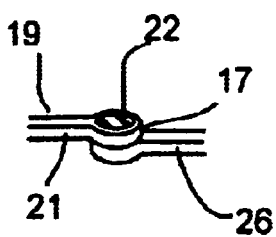
FIG. 4C is a detail of a riveted joint.

FIGS. 4A, 4B and 4C illustrate a riveted and pinned joint. The space frame 10 is comprised of flexible joints 16 and spacer arms 21. Each joint has two spacing arms, one at the top 21 and one at the bottom 26. The spacing arms form the linkage between joints. The joint eyelet 17 and spacing arm 21 may be formed as a single structure, 19. The eyelets 17 of two arms are aligned and held in place with a fastening means, e.g. a pin 18 or a rivet 22.

The number of joints in a frame can be varied according to the size and the degree of expansion that is desired for a particular use, although an even number of joints will generally be used. The compressed radius ($r_{col}$) of the frame, expanded radius ($r_{exp}$) of the frame, number of joints (n) and distance between two adjoining joints ($L_a$) have a straightforward geometric relationship, and can be used to calculate the degree of expansion ($E=(r_{exp}-r_{col})$) that will be achieved with a given number of joints. $L_a$ is roughly equal to the spacing arm length(s). In frames having an adjustable spacing arm length, that length should also be accounted for in the calculation.

In the case where the spacing arms are a continuous filament, the radius of the compressed frame is equal to $L_a$ plus the radius of the two joints, hence $r_{col}=L_a+2r_j$. When the frame is expanded, the circumference ($C_e$) will be equal to the number of joints multiplied by distance between joints, therefore $r_{exp}=n\ L_a/2\pi$. The degree of expansion can therefore be calculated as $$E = \frac{nL_a}{2\pi}(L_a + 2r_j)$$

To determine the appropriate geometry for a frame, one need only know the desired compressed radius and spacing arm length, degree of expansion, and joint radius to determine the number of joints that are required.

Figure 5A:
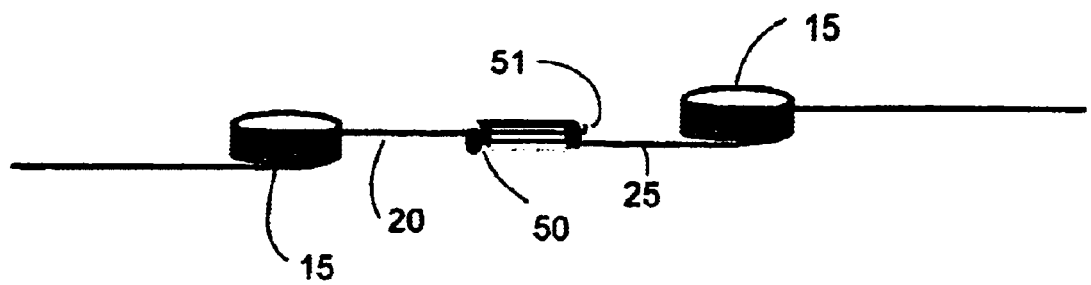
FIG. 5A is a detailed view of a sleeve attachment between two spacing arms, allowing for adjustment in the diameter of the frame, with a cutaway showing the overlapping position of the two spacing arms.

In some embodiments of the invention, the spacing arms are connected through an adjustable sleeve, as shown in FIG. 5A. To determine the degree of expansion in a frame where the distance between two joints can be adjusted in this way, the calculation must take into account the sleeve length, (w). If the assumption is made that all spacing arms are linked by a sleeve, and that E reflects the maximum expansion, then E is calculated as follows:

$$E = \frac{n(2L_a - w)}{2\pi(L_a + 2r_j)}$$

Figure 5B:
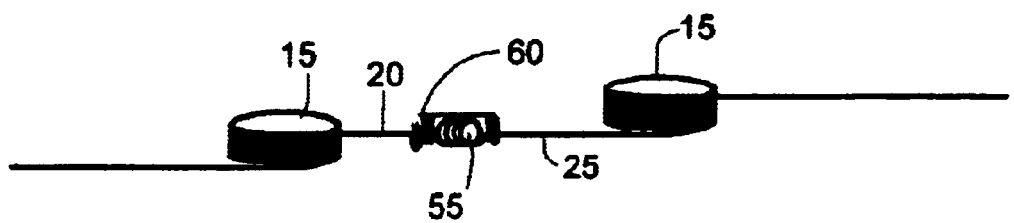
FIG. 5B is a detailed view of a compression spring attachment between spacing arms, with a sleeve covering.

In some embodiments of the invention, the spacing arms are connected through a compression spring encased in a sleeve, as shown in FIG. 5B. To determine the degree of expansion in a frame where there is a spring connection, the calculation must account for the spring length when compressed ($w_s$), and the fully expanded length of the spring (w), assuming that the fully expanded spring length is equal to the length of the sleeve. Again making the assumption that all spacing arms are connected in this way, and that E reflects the maximum expansion, then E is calculated as follows:

$$E = \frac{n[L_a + (w - w_s)]}{2\pi(L_a + 2r_j)}$$

The size of the frame can be widely varied, from a collapsed radius of less than 1 mm to a radius of several feet or more. As an example, for use in a stent, (making the assumption for simplicity that the spacing arms are a continuous filament) one might want a compressed radius of 1 mm, in order to easily accommodate delivery to the site of placement. The expanded radius, 5 mm is determined by the size of the vessel to be repaired. The frame will therefore have an expansion (E) of 5, using 40 spring joints with a radius of 0.1 mm, and spacing arms that are 0.8 mm in length.

The spacing arms between two springs can be joined by a variety of means. In one embodiment of the invention, the two arms are continuous, joined by any convenient method, e.g. formed from a continuous filament material, welded together, glued, etc. to provide a single spacing element between two joints, as shown in FIG. 1A.

Alternatively, the connection between spacing arms can be exploited to provide additional features. The arms may be joined by encasing two overlapping arms in a sleeve, as shown in FIG. 5A. The upper spacing arm 20 of a joint 15 overlaps with the lower spacing arm 25 of an adjoining joint 15. At the point of overlap, the two arms are encased in a sleeve 50. The spacing arms extend through the sleeve 50 and have a "stop" 51 at the end to prevent them from sliding out of the sleeve. The sleeve comprises a close-fitting member that holds the two arms in position, but allows for sliding of the arms past each other in order to further expand or contract the frame circumference. The sleeve is usually tubular, but the cross-sectional geometry will be designed to accommodate the particular spacing arms, and may be rectangular, circular, oval, etc.

The sleeve allows a precise adjustment of frame size prior to its use and placement, by moving the arms in the sleeve to achieve the desired size. In addition, after the space frame is expanded, the diameter can be adjusted again, by moving the arms relative to each other within the sleeve. The adjustment may be from about 1 to 70% of the circumference of the frame. The sleeve adjustment mechanism may be present on one or more spacing arm connections for a frame, up to and including all of the spacing arms. In addition to providing a means of adjusting the expansion, the overlapping arm connection may serve other purposes. It can be used to increase the expansion ratio, E. It can also be used to encase the spacing arm joint so as to decrease turbulent flow, to increase biocompatibility, strengthen the frame, protect the spacing arms from damage due to external forces, etc.

The sleeve will usually extend from at least about 30% of the spacing arm length, up to as much as about 95% of the spacing arm length, usually not more than about 90% of the spacing arm length. The sleeve may be constructed of any biocompatible metal; plastic; fabric; film, e.g. ePTFE, dacron, etc. The sleeve may be optionally coated to decrease thrombogenicity, e.g. with heparin, and increase biocompatibility. For example, the overlap between two spacing arms may be wrapped with a sheet of metal or fabric which is secured along its length by glue, welding, etc.

Shown in FIG. 5B, the spacing arms 20 and 25 can be joined through a compression spring 55, to provide flexibility in the frame. Preferably, a sleeve 60 is used to encase the springs. The sleeve is similar in design to the sleeve 50, but may be looser fitting, as it is not necessary to hold the arms in place. The spring spacer can be used where a continuous frame structure is desired. It can be used as a parameter to affect the circumferential stiffness of the frame, i.e. the stiffness of the compression springs may be chosen to tailor the circumferential stiffness of the frame. The materials for the sleeve are typically as those described above. The length of the sleeve will usually be at least about the desired expansion length of the spring, and may extend up to the full length of the distance between the two joints.

Figure 6A:
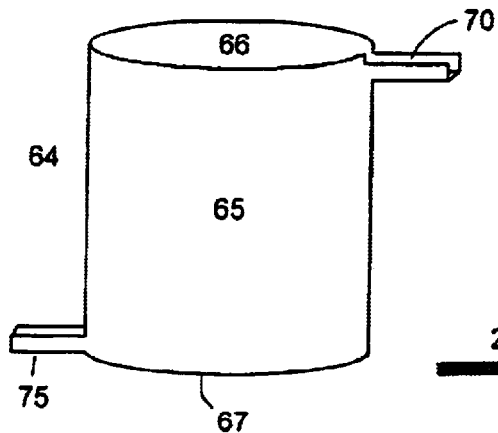
FIG. 6A shows a locking sleeve for a spring junction. The position of the spring is shown in FIG. 6B and FIG. 6C.

The spacing arms may be locked in position with a sleeve, which will ensure that the spacing arms are kept at a fixed angle apart. FIGS. 6A to 6D illustrate a locking mechanism 64 for a spring joint. FIG. 6A shows a sleeve, 65, which encases the spring 15. The sleeve 65 is a tubular member, with a cross-sectional geometry suitable for the shape of the spring, e.g. circular, oval, rectangular, etc. As shown in the drawing it is open at the top 66 and bottom 67, although the bottom 67 may be closed, as the bottom of the spring is always locked in place. Attached to the sleeve are supports 70 and 75 for the spacing arms. The supports 70 and 75 are essentially in the form of a channel, which is open along its length to form a continuous opening with the sleeve 66 and 67, respectively.

Figure 6B:
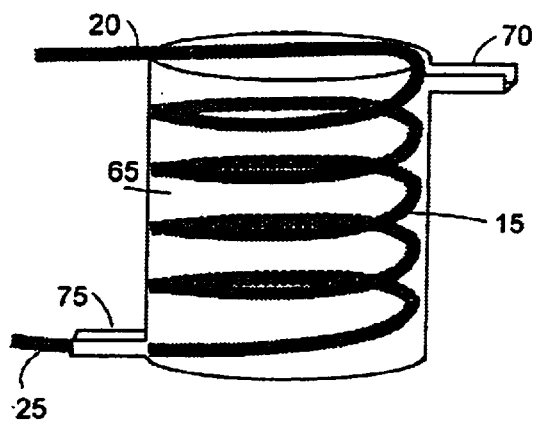
FIG. 6D is a top view of the locking mechanism, showing the angle at which the arms are locked.
Figure 6C:
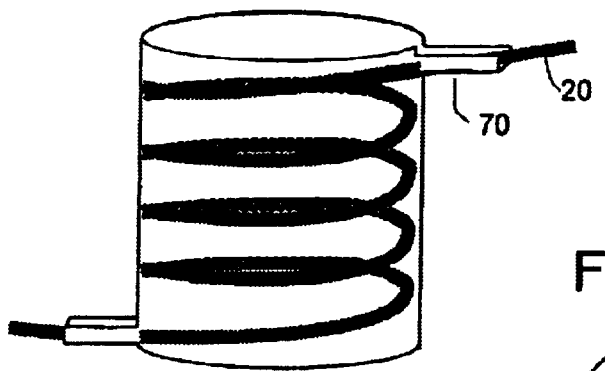
Figure 6D:
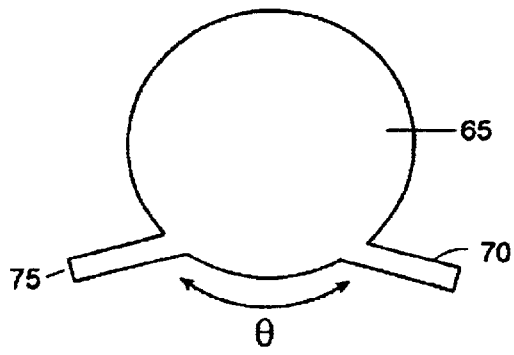

FIG. 6B is a side view that illustrates when the spring is in a parallel configuration (refer to FIG. 2C), the upper arm of the spring 20 rests on the top of the sleeve 65. The spring is stretched inside the sleeve, and the bottom arm of the spring 25 is fixed inside the bottom support 75. FIG. 6C shows that when the spring is moved to an antiparallel configuration (refer to FIG. 1B) the upper arm 20 is fixed inside the top support 70 and the bottom arm 25 is fixed inside the bottom support 75. The angle at which the arms are fixed, θ, (shown in FIG. 6D) may be any angle, usually not less than about 90° and not more than 300°, more usually not less than about 180° and not more than about 270°.

The locking mechanism 64 will closely fit around the spring. It will typically be of a stiff material, which will not be deformed by the tension of the spring. Suitable materials include any biocompatible metal or plastic.

Figure 7A:
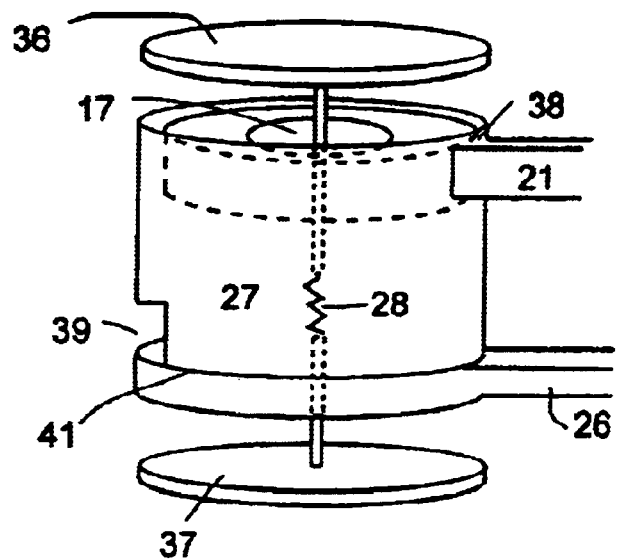
FIG. 7A and FIG. 7B show a locking mechanism for a pinned joint in the parallel and anti-parallel configuration, respectively.
Figure 7B:
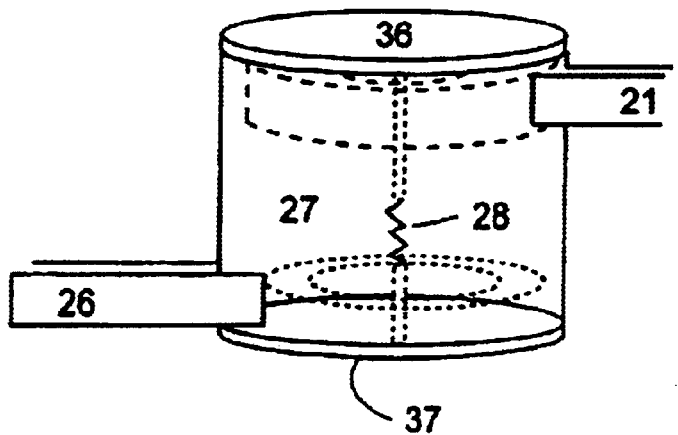

A locking mechanism for a pinned or riveted joint is shown in FIG. 7A and FIG. 7B. The mechanism comprises a fastening means 36 and 37, e.g. rivets or pins; a shaft 27 and an extensional spring 28. The shaft has cut-outs at the top 38 and the bottom 39. The upper spacing arm 21 always extends through the top cut-out 38 and is always fixed in place. The upper fastening means 36 always rests on the top of the shaft 27. When the frame is in a compressed configuration, shown in FIG. 7A, with the arms oriented to be parallel, the spring 28 is extended to allow the lower arm 26 to rest on the lip of the shaft 41. The lower fastening means 37 rests on the bottom of the eyelet of the lower arm 26. When the frame is in an expanded configuration, shown in FIG. 7B, with the arms oriented to be anti-parallel, the spring 28 is less extended because it has pulled the lower arm 26 into the bottom cut-out 39. The lower fastening means 37 now rests on the bottom of the shaft 27, closing off the bottom of the shaft 27.

Figure 8A:
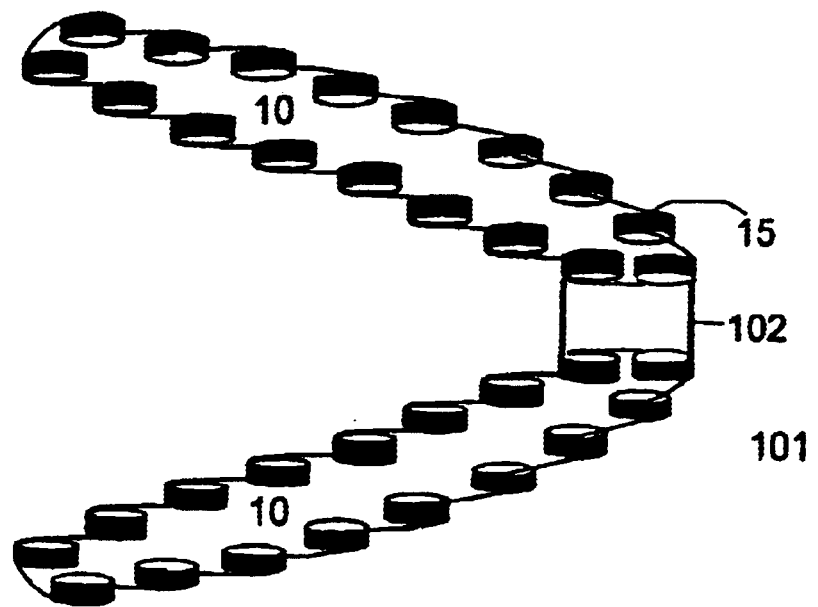
FIG. 8A, FIG. 8B and FIG. 8C show linked stents constructed of multiple frames.
Figure 8B:
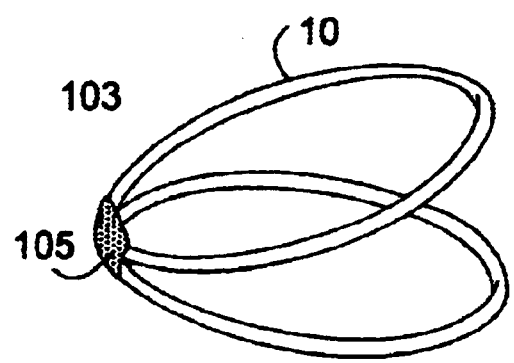
Figure 8C:
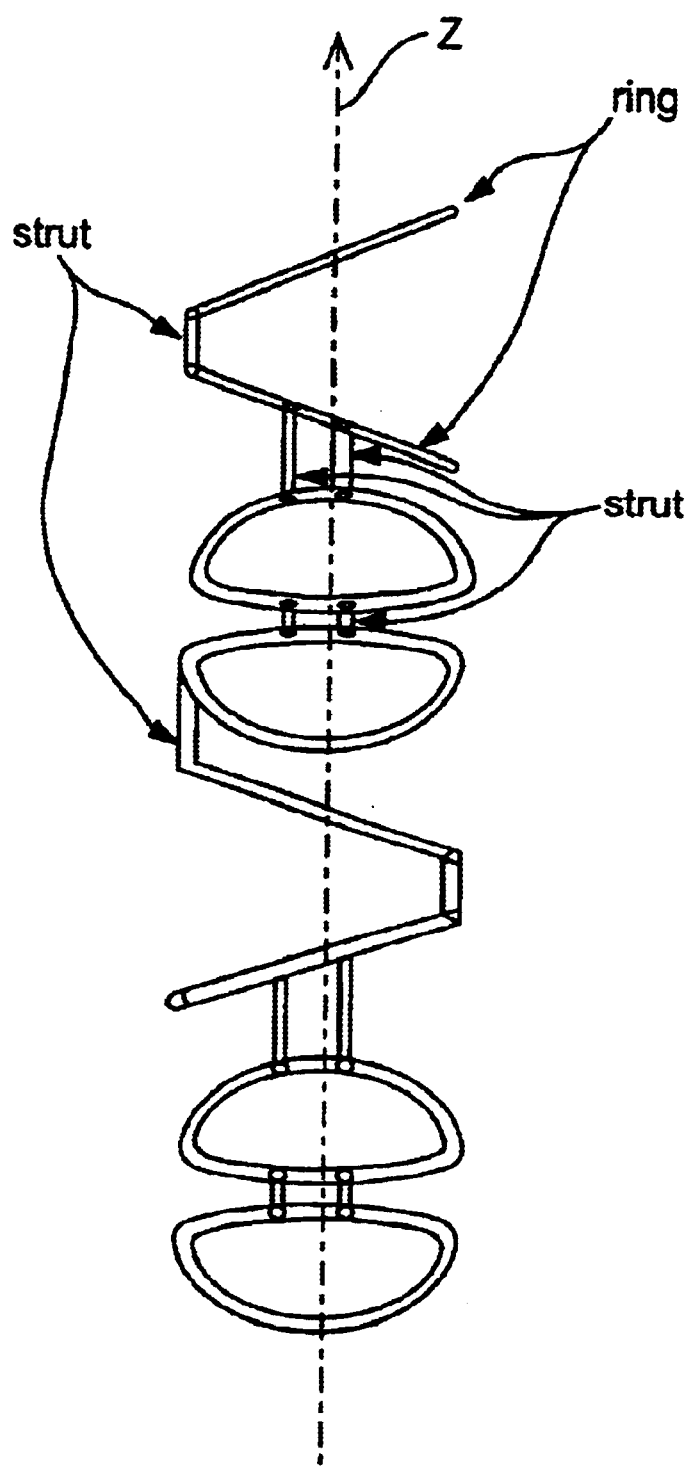

The basic space frame finds particular utility in the manufacture of stents. A series of individual frames are linked to each other to form a linked stent, as shown in FIG. 8A, FIG. 8B and FIG. 8C. Two or more frames are linked to longitudinal struts to form the support structure for a strutted stent, shown in FIG. 9. A strutted stent can also be formed by fixing longitudinal struts to the spiral structure shown in FIG. 11. The stents formed from the expandable space frame can be designed to have a number of additional features.

Other utilities for the subject frame include astronautics. Spacecraft or satellites often employ expandable structures because storage space during launch is limited. The expandable structures used in space could be as small as several centimeters and length, to as large as several meters in diameter and length. The frame and stent-like devices are useful to repair piping in construction and/or machinery that is difficult to access. The repair method is analogous to surgical techniques, i.e. the device in compressed in diameter and snaked into the proper position, at which point it is deployed. The device could also be used for tent construction, e.g. for military or recreational purposes, where it is desirable to use minimal space when packed.

Composition of the Frame

In its simplest form, the space frame is comprised of flexible joints and spacing arms. The flexible joint may be a spring, or other joints as previously described. The coils of a spring and the spacing arms are typically formed from wire or filament, where filament may encompass any suitable material. The entire frame can be formed from a single filament, if desired, or the joints and spacing arms may be separately formed and attached by any suitable method as known in the art. Filaments may have any cross-sectional geometry, e.g. square, round oval, triangular, etc. The springs and arms may be made of the same or different material, and combinations of materials may be used, e.g. alternating springs may be formed from different materials. The arms may also be variable in length, or may be of equal lengths. Where the flexible joints are pinned or riveted joints, the spacing arm and eyelet may be a single molded piece, or separate molded pieces which are then glued, welded, etc.

For use in stents, the frame will be formed from biologically compatible materials. Biologically compatible metals include stainless steel, titanium, tantalum, gold, platinum, copper and the like, as well as alloys of these metals. Low shape memory plastic may also be used. Alternatively the filament is formed from a shape-memory plastic or alloy, such as nitinol, which automatically transforms from one shape to another as its temperature passes through a critical point.

Diameter of the filament or formed pieces will vary widely depending on the use of the frame. For the manufacture of stents, a filament will range from about 0.05 mm to 0.15 mm in diameter for stents in relatively small coronary arteries, to as large as about 0.5 mm diameter for stents used in much larger abdominal aorta. Stents for use in larger vessels, e.g. trachea, may use filaments of a larger diameter. The cross-section of a filament need not be constant along its entire length, but may include portions having a larger or smaller cross-section as desired.

Springs of varying sizes are commercially available. Each spring will have at least one coil, usually multiple coils. The number of coils will determine both the degree of offset in the frame, and the stiffness of the spring. The stiffness of the spring will vary with the specific use of the frame. By selecting the appropriate material and spring stiffness, the overall radial stiffness of the frame can be tailored to the desired use.

The radius of the spring will also vary with the desired use of the frame. For use in coronary stents, the radius will usually be at least about 1.5 mm, and may be as large as 15 mm. The height of the spring, i.e. the height of the stacked coils, will range from 0.10 mm to 1 mm for coronary stents.

Where the spacing arms or springs are encased in a sleeve, the sleeve will typically be formed from a sheet or tube of a material that is compatible with the filaments used in the rest of the frame, as previously discussed.

Stent Design

As discussed above, an important use for the space frame is in the manufacture of stents for the support of biological tissues in situ. Stents are commonly used to open blood vessels, e.g. clearing obstructions, and to repair damage to vascular tissues, e.g. arteries and veins. Two different types of stent design may utilize the space frame: a linked stent and a strutted stent. The stents are used conventionally, for preventing restenosis or other narrowing of vessels, to provide support for the vessel at the site of an aneurysm or other weakening of the vessel wall. The use of stents for the support of blood vessels is well known in the art and need not be further elaborated here. A modification of stents where there is a flexible cover attached to the stent frame is commonly referred to as stent graft. The purpose of stent grafts is to seal off vascular abnormalities, such as aneurisms.

In addition to blood vessels, other vessels of the body may be repaired with a stent, including the trachea for breathing disorders, renal and urethral tubules, fallopian tubes for the treatment of infertility, eustachian tubes for the treatment of chronic ear infection and other hearing disorders, large and small intestines, etc. The stent design is not limited to any particular body tissue, but will be manufactured with a size, expansion, and radial stiffness suitable for the different purposes.

The recipient for the stent may be any mammalian species, including canines; felines; equines; bovines; ovines; etc. and primates, particularly humans. Animal models, particularly small mammals, e.g. murine, lagomorpha, etc. are of interest for experimental investigations.

The stents are useful for any vascular surgery, such as may be used in any situation in which the flow of blood through a vessel has been compromised. There are a variety of conditions where there is restricted blood flow through that vessel. Occlusive vascular conditions of interest include atherosclerosis, graft coronary vascular disease after transplantation, vein graft stenosis, peri-anastomatic prosthetic graft stenosis, restenosis after angioplasty, coronary artery disease, peripheral vascular disease or other forms of occlusive arterial disease, and the like.

Any convenient method for the placement of the stent may be used. As known in the art, a stent is inserted into a catheter for delivery in a non-expended condition. In one embodiment of the invention, wires 200 and 201 are threaded through the centered springs 30 and 31, as shown in FIG. 2B, in order to hold the frame in the compressed form. The catheter is used to thread the stent through the vasculature, to the site for placement. The stent is then pushed or otherwise maintained in position while the catheter is withdrawn. When a holding wire is used, the wire is then removed to allow expansion of the frame(s).

Where spring joints are used, in the initial placement of the stent it will self-expand to a pre-determined diameter. A frame formed from pinned or riveted joints will be expanded by balloon catheter, as is well-known in the art.

In some cases, it may be desirable for the stent to continue to expand after the insertion procedure is performed. The stent configuration with an adjustable diameter, utilizing a sleeve to hold overlapping spacing arms, addresses this problem. A balloon catheter may be positioned inside the stent in situ after the original placement, and used to further expand the diameter. If compression springs are used to link the spacing arms, then the stent will continue to self-expand in situ as much as the vessel will allow, or until it reaches the maximum diameter.

An optional feature for stents or stent grafts is the addition of "barbs" or needles facing outward from the frame, to anchor the stent in place. Barbs may be attached to the spacing arms, sleeves, or springs. The barbs will be of sufficient length to penetrate the walls of the vessel, but will not be so long that they protrude out through the vessel outer wall. The number of barbs is variable, but when present will usually be at least two, on opposite sides of the frame.

Stents will generally have an overall length of from about 2 mm to about 200 mm. Stents, such as may be used to prevent narrowing of blood vessels, are usually from about 2 to 100 mm in length. Stent grafts, such as may be used to repair an aneurysm, are generally longer, and will usually range from about 50 to 200 mm in length.

The linked stent is formed by linking two or more space frames, as shown in FIGS. 8A to 8C. A frame 10 is joined to a second frame 10 through a flexible linkage means. A plurality of frames may be linked in this manner. The number of frames to be linked is determined by length of vessel wall to be repaired. The linkages can be one or two flexible struts located on the coil, on the spacing arms, or on the sleeves that join the spacing arms. Alternatively, the linkage can be a flexible membrane that links the spacing arms. The struts or membranes can be of any desired flexibility, and may even be very rigid, depending on the application. For stents and stent-grafts, a high degree of flexibility is desirable.

For stents, the length of space to be repaired may be between about 2 mm and 200 mm. This would require from between about 3 to 300 linked frames, depending on the height of the joints.

FIG. 8A shows a linked stent 101 formed by joining two frames 10 linked through two struts 102 connected at the spring joints 15. The struts are joined to the frames by any convenient method, e.g. glue, welding, etc. The struts may be formed of any biocompatible metal or plastic that is compatible with the material used in the frames. The struts in such an embodiment are typically short, and will be closely positioned on the frame perimeter, as shown in the drawing. The struts are typically at least about 0.1 mm, usually at least about 0.5 mm, and not more than about 5 mm, usually not more than about 2 mm. The struts do not necessarily have to be the same length throughout the linked structure.

FIG. 8B shows an alternative linked stent 103 formed by joining two frames 10 with a flexible sleeve 105 that fits over two frames. The figure has omitted details of the frame, and is drawn with exaggerated diameter for clarity.

The linked stents in both FIG. 8A and FIG. 8B will frequently join the "top" of a frame with the "bottom" of a second frame, and so on with a third, fourth, etc. frame. However, to achieve maximum flexibility in all directions along the length of the stent, a slightly different configuration is required, as shown in FIG. 8C.

FIG. 8C shows a flexible linked stent formed of dimer frames, such as 101 or 103 in FIGS. 8A and 8B. For convenience, the dimer linkage is shown 105 as a single element. The next element 106 is rotated 90 degrees about the z-axis and then linked 107 to the first element 105. The following element 108 is rotated 90 degrees about the z-axis again and linked 109 to the previous element 106.

For both the linked stent and the strutted stent, the orientation of each frame along the length of the structure can be completely independent of the other frames. However, frames that are adjacent along the length of the structure will most likely be either "in-sync" (in phase), completely "out-of-sync" (180 degrees out of phase), or half-way between the two (90 degrees out of phase). As an example of in phase, the bottom of a "down staircase" of one frame is linked to the bottom of a "down-staircase" of the adjacent frame. An example of 180 degrees out of phase would link the bottom of a "down-staircase" to the top of an "up-staircase" of an adjacent frame. A 90 degrees out of phase would link the bottom of a "down-staircase" to the middle of either an "up- or down-staircase" of the adjacent frame.

Most conventional stents undergo longitudinal shortening when there is an increase in diameter, creating a problem of movement against the vessel wall. It is therefore desirable to minimize longitudinal shortening, both to prevent tissue damage in situ, and to improve deployment accuracy. The subject design addresses this problem by having a constant longitudinal length when the strutted stent is expanded in diameter.

Figure 9A:
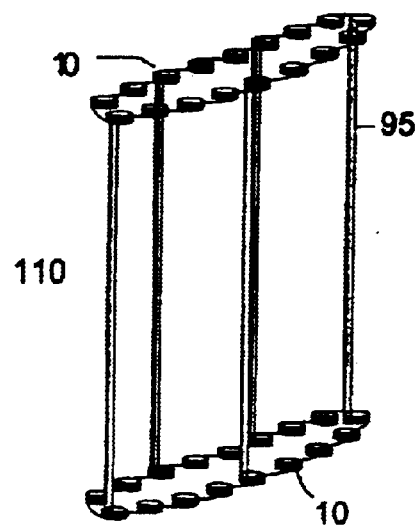
FIG. 9A is a side view of a strutted stent formed from space frames linked by longitudinal struts.

A strutted stent 110 is shown in FIG. 9A. Two or more space frames 10 are linked by longitudinal struts 95. An alternate form of the strutted stent is realized by fixing one or more longitudinal struts to the spiral structure shown in FIG. 11A. The struts can be attached through the coils of the springs or can be welded to the spacing arms or to the sleeves that join the spacing arms. They can be attached with a fastener, or they can be welded, glued, etc. The struts may be any flexible biocompatible material, e.g. plastics, metals, etc. The stiffness of the strut is an important consideration, as it should be flexible enough to be placed in curved vessels, as is typical for arteries and veins.

For use in a strutted structure to be used as a stent or stent-graft, the length of a strut will usually range from about 2 to 200 mm. The strut length will be partly determined by the number of frames placed along the length of the structure. There will usually be at least 2 frames, and not more than about 10 frames. The number of struts employed will depend on the desired stiffness of the stent, but generally will have at least three to four struts.

Figure 9B:
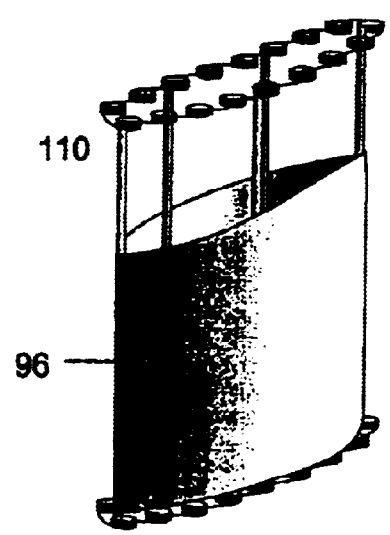
FIG. 9B shows the strutted stent covered with a flexible sock.

The stent, particularly a strutted stent, may be covered with a "sock", or graft, of flexible material, as known in the art. FIG. 9B shows a strutted stent 110 with a cut-away view of a flexible sock 96. The sock may be completely on the inside of the frame; completely outside the frame; or woven in between the struts. Conveniently, the sock is attached with stitches or glue. The sock forms a synthetic vessel, where the vessel is a tubular member usually having a substantially uniform bore. Suitable materials for the vessel include, for example, expanded polytetrafluoroethylene (e-PTFE) and dacron. High porosity ePTFE may be used for some purposes, where the slit-like fissures in the vessel well are in the range of 90 μm in size. For vascular repair, the vessel will generally be at least about 1 mm in internal diameter, more usually at least about 15 to 25 mm in diameter, and not more than about 50 mm in diameter.

To reduce the thrombogenicity of the graft, the vessel may be sodded or seeded with endothelial cells. Sodding procedures place the cells directly onto the polymeric internal surface of the vessel as well as into the interstices of the vessel, generally under mild pressure. For example, one termini of the vessel may be clamped, and the cells injected with a syringe through the open end. The vessel is porous to water, and so the media is forced through the interstices of the wall, while the cells are retained.

Seeding procedures mix the cells with blood or plasma, and then add to the vessel during the pre-clotting period. There are several versions of the technique known as seeding. The synthetic grafts can be coated with collagen or fibronectin prior to the addition of endothelial cells into the lumen. The synthetic graft is then incubated in vitro with rotation to allow the binding of the endothelial cells to the luminal surface. After several hours or days culture, the graft can be implanted. Alternatively, autologous blood can be forced under pressure through the interstices of the synthetic graft to allow retention of blood cells and protein onto and into the graft prior to addition of the endothelial cells (either passively are actively under pressure). A third alternative is to mix the endothelial cells with the blood prior to the application onto and into the graft.

Endothelial cells may be genetically modified to express factors that encourage the growth of endothelial cells, e.g. VEGF; PlGF; TGF-β1; aFGF and bFGF; and hepatocyte growth factor; or a protein that inhibits the growth of intimal cells, for example, inducible nitric oxide synthase (iNOS) or endothelial cell nitric oxide synthase (ecNOS). Proteins that inhibit thrombosis, e.g. tissue plasminogen activator (tPA), urokinase, and streptokinase, are also of interest.

Alternatively, the stent may include a reservoir of biologically active materials, e.g. antibiotics, anti-thrombogenic factors, growth factors, etc. Such a reservoir may be a coating on the stent filaments, embedded in plastics or the graft, deposited as a gel inside the spring coils, etc. Often stent grafts are impregnated with biocompatible substances are coated with heparin or hydrogel.

It is contemplated that a kit may be provided for the use of the stent in medical procedures. Such a kit may include two or more of the following: a stent, optionally wired in a compressed configuration, a sock for a stent-graft, and a catheter for insertion of the stent. The compressed stent may be pre-loaded into the catheter for ease of use.

It is evident that the subject invention provides for a frame that allows a high degree of expansion from a compressed configuration, while maintaining flexibility and conformability. The frame forms the basis of a number of structures having utility in medical and other applications.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. The examples are put forth so as to provide those of ordinary skill in the art with a complete disclosure and description of how to make and use the subject invention, and are not intended to limit the scope of what is regarded as the invention.

What is claimed is:

1. An expandable frame and wire for deployment in a body lumen, comprising:
   a plurality of flexible torsion spring joints linked by spacing arms with said torsion spring joints and spacing arms when in an expanded state defining an open structure surrounding and spaced from a longitudinal axis; at least alternate ones of said flexible torsion spring joints movable radially inwardly toward said longitudinal axis to define a structure with a inner plurality of said flexible torsion spring joints in close proximity to said axis and with a remaining plurality of said flexible torsion spring joints disposed radially spaced outwardly from said inner plurality and with said inner and outer plurality connected by said spacing arms extending substantial radially from said axis
   wherein said expandable frame is in a compressed configuration as a result of moving alternating flexible torsion spring joints to a center of the frame, and comprises at least one wire threaded through a flexible torsion spring joint in said center of the frame.

2. The expandable frame according to claim 1, wherein said frame is a circular frame.

3. The expandable frame according to claim 1, wherein said torsion springs are enclosed by a locking mechanism.

4. The expandable frame according to claim 1, wherein said spacing arms are continuous.

5. The expandable frame according to claim 1, wherein at least one pair of said spacing arms between two adjoining joints are overlapping and encased in a sleeve, said overlap being adjustable to provide for variable spacing between adjoining joints.

6. The expandable frame according to claim 5, wherein all of said offset spacing arms in said frame are overlapping and encased in a sleeve.

7. The expandable frame according to claim 1, wherein at least one pair of said spacing arms between two adjoining joints are linked by a compression spring and encased in a sleeve.

8. The expandable frame according to claim 7; wherein all of said spacing arms in said frame are linked by a compression spring and encased in a sleeve.

9. The expandable frame according to claim 1, wherein said number of joints is at least about 64.

10. The expandable frame according to claim 9, wherein said frame in said compressed configuration has a diameter of less than about 5 mm.

11. The expandable frame according to claim 1, wherein said frame is a spiral frame comprising from 3 to 200 spiral units.

12. The expandable frame according to claim 11, wherein said spiral frame comprises from 10 to 20 spiral units.

* * * * *